US010702257B2

(12) United States Patent
Hess et al.

(10) Patent No.: US 10,702,257 B2
(45) Date of Patent: Jul. 7, 2020

(54) POSITIONING DEVICE FOR USE WITH SURGICAL INSTRUMENTS

(71) Applicant: Ethicon Endo-Surgery, LLC, Guaynabo, PR (US)

(72) Inventors: Christopher J. Hess, Blue Ash, OH (US); Frederick E. Shelton, IV, Hillsboro, OH (US); Jeffrey L. Savage, West Chester, OH (US); Craig T. Gates, West Chester, OH (US); Douglas E. Withers, Cincinnati, OH (US); Adam D. Hensel, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 814 days.

(21) Appl. No.: 14/868,634

(22) Filed: Sep. 29, 2015

(65) Prior Publication Data
US 2017/0086813 A1 Mar. 30, 2017

(51) Int. Cl.
*A61B 17/02* (2006.01)
*A61B 17/34* (2006.01)
*A61B 17/00* (2006.01)

(52) U.S. Cl.
CPC ...... *A61B 17/0218* (2013.01); *A61B 17/3403* (2013.01); *A61B 17/3462* (2013.01);
(Continued)

(58) Field of Classification Search
CPC ............ A61B 17/0218; A61B 17/3403; A61B 17/3462; A61B 17/02; A61B 17/0293;
(Continued)

(56) References Cited

U.S. PATENT DOCUMENTS 2,898,068 A * 8/1959 Warren ................. B23Q 1/28
248/183.1
3,043,309 A 7/1962 McCarthy
(Continued)

FOREIGN PATENT DOCUMENTS

DE 101 49 421 A1 4/2003
EP 1 709 900 A1 10/2006
(Continued)

OTHER PUBLICATIONS

[No Author Listed] "The Evolution of Minimally Invasive Surgery," Stryker Korea. MiniLap Product Brochure. 4 pages. Publication date likely at least as early as Dec. 2013, based upon Dec. 2013 510(k) Clearances listed at [http://www.fda.gov/MedicalDevices/ProductsandMedicalProcedures/DeviceApprovalsandClearances/510kClearances/ucm380398.htm], No. K132232.
(Continued)

*Primary Examiner* — David W Bates
(74) *Attorney, Agent, or Firm* — Mintz Levin Cohn Ferris Glovsky and Popeo, P.C.

(57) ABSTRACT

Devices and methods for positioning a surgical instrument are described herein. In one embodiment, a positioning device can include a base that can be placed against tissue and a shuttle including a lumen that can receive a surgical instrument. The lumen can be translated in at least two directions relative to the base and an orientation of the lumen relative to the base can be polyaxially adjusted. Further, the device can include a locking mechanism that, upon actuation, prevents both translational movement and polyaxial movement of the lumen relative to the base.

20 Claims, 11 Drawing Sheets

(52) U.S. Cl.
CPC ............... *A61B 2017/00951* (2013.01); *A61B 2017/3407* (2013.01); *A61B 2017/347* (2013.01); *A61B 2017/3427* (2013.01)

(58) Field of Classification Search
CPC .......... A61B 17/0206; A61B 17/00477; A61B 2017/00951; A61B 2017/3407; A61B 2017/3427; A61B 2017/347; A61B 1/32; A61B 1/018; A61B 90/11; A61B 90/50; A61B 90/10; A61B 2090/101; A61B 2090/103; A61B 34/20; A61B 17/3407; A61B 17/347; A61M 5/00
USPC ................... 600/227, 130; 604/385.06, 116; 606/129, 130; 269/78, 72
See application file for complete search history.

(56) References Cited

U.S. PATENT DOCUMENTS

| | | | |
|---|---|---|---|
| 3,078,577 A * | 2/1963 | Prentki | A61C 11/02 433/60 |
| 3,196,875 A * | 7/1965 | Pfeiffer | A61B 90/11 248/286.1 |
| 3,358,676 A | 12/1967 | Frei et al. | |
| 3,710,399 A | 1/1973 | Hurst | |
| 3,893,448 A | 7/1975 | Brantigan | |
| 3,906,217 A | 9/1975 | Lackore | |
| 3,988,535 A | 10/1976 | Hickman et al. | |
| 4,047,136 A | 9/1977 | Satto | |
| 4,063,561 A | 12/1977 | McKenna | |
| 4,099,192 A | 7/1978 | Aizawa et al. | |
| 4,278,077 A | 7/1981 | Mizumoto | |
| 4,384,584 A | 5/1983 | Chen | |
| 4,585,282 A | 4/1986 | Bosley | |
| 4,597,390 A | 7/1986 | Mulhollan et al. | |
| 4,655,746 A | 4/1987 | Daniels et al. | |
| 5,030,223 A * | 7/1991 | Anderson | A61B 90/11 600/383 |
| 5,052,402 A | 10/1991 | Bencini et al. | |
| 5,201,743 A | 4/1993 | Haber et al. | |
| 5,230,628 A * | 7/1993 | Kaneko | G09B 19/0053 358/400 |
| 5,282,806 A | 2/1994 | Haber et al. | |
| 5,286,255 A | 2/1994 | Weber | |
| 5,308,357 A | 5/1994 | Lichtman | |
| 5,314,424 A | 5/1994 | Nicholas | |
| 5,330,502 A | 7/1994 | Hassler et al. | |
| 5,352,219 A | 10/1994 | Reddy | |
| 5,375,588 A * | 12/1994 | Yoon | A61B 17/3403 600/114 |
| 5,392,917 A | 2/1995 | Alpern et al. | |
| 5,417,203 A | 5/1995 | Tovey et al. | |
| 5,441,059 A | 8/1995 | Dannan | |
| 5,468,250 A | 11/1995 | Paraschac et al. | |
| 5,502,698 A | 3/1996 | Mochizuki | |
| 5,507,297 A | 4/1996 | Slater et al. | |
| 5,540,648 A | 7/1996 | Yoon | |
| 5,562,655 A | 10/1996 | Mittelstadt et al. | |
| 5,578,052 A | 11/1996 | Koros et al. | |
| 5,593,402 A | 1/1997 | Patrick | |
| 5,613,937 A | 3/1997 | Garrison et al. | |
| 5,618,303 A | 4/1997 | Marlow et al. | |
| 5,716,326 A | 2/1998 | Dannan | |
| 5,762,255 A | 6/1998 | Chrisman et al. | |
| 5,776,143 A * | 7/1998 | Adams | A61B 90/11 606/130 |
| 5,792,165 A | 8/1998 | Klieman et al. | |
| 5,810,877 A | 9/1998 | Roth et al. | |
| 5,881,615 A | 3/1999 | Dahl et al. | |
| 5,928,263 A | 7/1999 | Hoogeboorn | |
| 5,980,455 A | 11/1999 | Daniel et al. | |
| 5,984,930 A * | 11/1999 | Maciunas | A61B 90/11 600/417 |
| 6,024,748 A | 2/2000 | Manzo et al. | |
| 6,059,719 A | 5/2000 | Yamamoto et al. | |
| 6,099,537 A | 8/2000 | Sugai et al. | |
| 6,159,200 A | 12/2000 | Verdura et al. | |
| 6,309,397 B1 | 10/2001 | Julian et al. | |
| 6,315,789 B1 | 11/2001 | Cragg | |
| 6,419,688 B1 | 7/2002 | Bacher et al. | |
| 6,471,172 B1 | 10/2002 | Lemke et al. | |
| 6,589,211 B1 | 7/2003 | MacLeod | |
| 6,595,984 B1 | 7/2003 | DeGuillebon | |
| 6,626,824 B2 | 9/2003 | Ruegg et al. | |
| 6,635,071 B2 | 10/2003 | Boche et al. | |
| 6,723,043 B2 | 4/2004 | Kleeman et al. | |
| 6,770,081 B1 | 8/2004 | Cooper et al. | |
| 6,776,165 B2 | 8/2004 | Jin | |
| 6,827,712 B2 | 12/2004 | Tovey et al. | |
| 6,860,878 B2 | 3/2005 | Brock | |
| 6,869,395 B2 | 3/2005 | Page et al. | |
| 6,884,213 B2 | 4/2005 | Raz et al. | |
| 6,936,003 B2 | 8/2005 | Iddan | |
| 6,942,674 B2 | 9/2005 | Belef et al. | |
| 6,986,738 B2 | 1/2006 | Glukhovsky et al. | |
| 6,994,708 B2 | 2/2006 | Manzo | |
| 7,039,453 B2 | 5/2006 | Mullick et al. | |
| 7,042,184 B2 | 5/2006 | Oleynikov et al. | |
| 7,066,879 B2 | 6/2006 | Fowler et al. | |
| 7,083,579 B2 | 8/2006 | Yokoi et al. | |
| 7,122,028 B2 | 10/2006 | Looper et al. | |
| 7,125,403 B2 | 10/2006 | Julian et al. | |
| 7,169,104 B2 | 1/2007 | Ueda et al. | |
| 7,199,545 B2 | 4/2007 | Oleynikov et al. | |
| 7,211,094 B2 | 5/2007 | Gannoe et al. | |
| 7,241,290 B2 | 7/2007 | Doyle et al. | |
| 7,297,142 B2 | 11/2007 | Brock | |
| 7,331,967 B2 | 2/2008 | Lee et al. | |
| 7,429,259 B2 | 9/2008 | Cadeddu et al. | |
| 7,448,993 B2 | 11/2008 | Yokoi et al. | |
| 7,559,887 B2 | 7/2009 | Dannan | |
| 7,566,331 B2 | 7/2009 | Looper et al. | |
| 7,604,642 B2 | 10/2009 | Brock | |
| 7,651,471 B2 | 1/2010 | Yokoi et al. | |
| 7,666,181 B2 | 2/2010 | Abou El Kheir | |
| 7,678,043 B2 | 3/2010 | Gilad | |
| 7,691,103 B2 | 4/2010 | Fernandez et al. | |
| 7,691,126 B2 | 4/2010 | Bacher | |
| 7,699,835 B2 | 4/2010 | Lee et al. | |
| 7,722,599 B2 | 5/2010 | Julian et al. | |
| 7,862,553 B2 | 1/2011 | Ewaschuk | |
| 7,894,882 B2 | 2/2011 | Mullick et al. | |
| 7,901,398 B2 | 3/2011 | Stanczak et al. | |
| 8,021,358 B2 | 9/2011 | Doyle et al. | |
| 8,038,612 B2 | 10/2011 | Paz | |
| 8,052,636 B2 | 11/2011 | Moll et al. | |
| 8,057,502 B2 | 11/2011 | Maliglowka et al. | |
| 8,088,062 B2 | 1/2012 | Zwolinski | |
| 8,128,643 B2 | 3/2012 | Aranyi et al. | |
| 8,182,414 B2 | 5/2012 | Handa et al. | |
| 8,187,166 B2 | 5/2012 | Kuth et al. | |
| 8,377,044 B2 | 2/2013 | Coe et al. | |
| 8,397,335 B2 | 3/2013 | Gordin et al. | |
| 8,398,544 B2 | 3/2013 | Altamirano | |
| 8,409,076 B2 | 4/2013 | Pang et al. | |
| 8,475,361 B2 | 7/2013 | Barlow et al. | |
| 8,518,024 B2 | 8/2013 | Williams et al. | |
| 8,623,011 B2 | 1/2014 | Spivey | |
| 8,636,648 B2 | 1/2014 | Gazdzinski | |
| 8,721,539 B2 | 5/2014 | Shohat et al. | |
| 8,764,735 B2 | 7/2014 | Coe et al. | |
| 8,845,661 B2 | 9/2014 | D'Arcangelo et al. | |
| 9,142,527 B2 | 9/2015 | Lee et al. | |
| 9,282,879 B2 | 3/2016 | Farin et al. | |
| 9,308,011 B2 | 4/2016 | Chao et al. | |
| 9,408,628 B2 | 8/2016 | Altamirano | |
| 9,451,937 B2 | 9/2016 | Parihar | |
| 9,924,979 B2 * | 3/2018 | Chegini | A61B 17/7074 |
| 2001/0051766 A1 | 12/2001 | Gazdzinski | |
| 2002/0042607 A1 | 4/2002 | Palmer et al. | |
| 2003/0060702 A1 | 3/2003 | Kuth et al. | |
| 2003/0114731 A1 | 6/2003 | Cadeddu et al. | |
| 2004/0093039 A1 | 5/2004 | Schumert | |

(56) References Cited

U.S. PATENT DOCUMENTS

| | | | |
|---|---|---|---|
| 2004/0122446 A1* | 6/2004 | Solar | A61B 90/11 606/129 |
| 2004/0133235 A1 | 7/2004 | Bacher | |
| 2004/0152941 A1 | 8/2004 | Asmus et al. | |
| 2004/0167543 A1 | 8/2004 | Mazzocchi et al. | |
| 2004/0243146 A1* | 12/2004 | Chesbrough | A61B 90/11 606/130 |
| 2005/0033354 A1 | 2/2005 | Montalvo et al. | |
| 2005/0085697 A1 | 4/2005 | Yokoi et al. | |
| 2005/0119640 A1 | 6/2005 | Sverduk et al. | |
| 2005/0131396 A1 | 6/2005 | Stanczak et al. | |
| 2005/0165449 A1 | 7/2005 | Cadeddu et al. | |
| 2005/0215983 A1 | 9/2005 | Brock | |
| 2005/0250984 A1 | 11/2005 | Lam et al. | |
| 2005/0272972 A1 | 12/2005 | Iddan | |
| 2005/0272974 A1 | 12/2005 | Iddan | |
| 2005/0273139 A1 | 12/2005 | Krauss et al. | |
| 2005/0288555 A1 | 12/2005 | Binmoeller | |
| 2006/0079933 A1 | 4/2006 | Hushka et al. | |
| 2006/0149135 A1 | 7/2006 | Paz | |
| 2006/0184161 A1 | 8/2006 | Maahs et al. | |
| 2006/0190035 A1 | 8/2006 | Hushka et al. | |
| 2006/0195015 A1 | 8/2006 | Mullick et al. | |
| 2006/0229592 A1 | 10/2006 | Yokoi et al. | |
| 2006/0258905 A1 | 11/2006 | Kaji et al. | |
| 2007/0010709 A1 | 1/2007 | Reinschke | |
| 2007/0049966 A1 | 3/2007 | Bonadio et al. | |
| 2007/0073247 A1 | 3/2007 | Ewaschuk | |
| 2007/0093792 A1 | 4/2007 | Julian et al. | |
| 2007/0123748 A1 | 5/2007 | Meglan | |
| 2007/0156015 A1 | 7/2007 | Gilad | |
| 2007/0255100 A1 | 11/2007 | Barlow et al. | |
| 2007/0255273 A1 | 11/2007 | Fernandez et al. | |
| 2007/0270651 A1 | 11/2007 | Gilad et al. | |
| 2007/0299387 A1 | 12/2007 | Williams et al. | |
| 2008/0015413 A1 | 1/2008 | Barlow et al. | |
| 2008/0015552 A1 | 1/2008 | Doyle et al. | |
| 2008/0045003 A1 | 2/2008 | Lee et al. | |
| 2008/0140090 A1 | 6/2008 | Aranyi et al. | |
| 2008/0142005 A1 | 6/2008 | Schnell | |
| 2008/0154299 A1 | 6/2008 | Livneh | |
| 2008/0242939 A1 | 10/2008 | Johnston | |
| 2008/0243106 A1 | 10/2008 | Coe et al. | |
| 2008/0287926 A1 | 11/2008 | Abou El Kheir | |
| 2008/0312499 A1 | 12/2008 | Handa et al. | |
| 2009/0005636 A1 | 1/2009 | Pang et al. | |
| 2009/0005638 A1 | 1/2009 | Zwolinski | |
| 2009/0209947 A1 | 8/2009 | Gordin et al. | |
| 2010/0030184 A1* | 2/2010 | Boulis | A61B 17/0206 604/500 |
| 2010/0249700 A1 | 9/2010 | Spivey | |
| 2011/0040322 A1 | 2/2011 | Major | |
| 2011/0087265 A1 | 4/2011 | Nobis et al. | |
| 2011/0087266 A1 | 4/2011 | Conlon et al. | |
| 2011/0087267 A1 | 4/2011 | Spivey et al. | |
| 2011/0115891 A1 | 5/2011 | Trusty | |
| 2011/0208007 A1 | 8/2011 | Shohat et al. | |
| 2011/0230869 A1 | 9/2011 | Altamirano | |
| 2011/0288560 A1 | 11/2011 | Shohat et al. | |
| 2012/0053402 A1 | 3/2012 | Conlon et al. | |
| 2012/0053406 A1 | 3/2012 | Conlon et al. | |
| 2012/0053573 A1* | 3/2012 | Alksnis | A61B 17/3403 606/1 |
| 2012/0065627 A1 | 3/2012 | Ghabrial et al. | |
| 2012/0078290 A1 | 3/2012 | Nobis et al. | |
| 2012/0078291 A1 | 3/2012 | Nobis et al. | |
| 2012/0083826 A1 | 4/2012 | Chao et al. | |
| 2012/0088965 A1 | 4/2012 | Stokes et al. | |
| 2012/0089093 A1 | 4/2012 | Trusty | |
| 2012/0095298 A1 | 4/2012 | Stefanchik et al. | |
| 2012/0259325 A1 | 10/2012 | Houser et al. | |
| 2012/0316575 A1 | 12/2012 | Farin et al. | |
| 2013/0138091 A1 | 5/2013 | Coe et al. | |
| 2014/0005474 A1 | 1/2014 | Farin et al. | |
| 2014/0066711 A1 | 3/2014 | Farin et al. | |
| 2014/0088569 A1 | 3/2014 | Parihar et al. | |
| 2014/0088637 A1 | 3/2014 | Parihar et al. | |
| 2014/0088638 A1 | 3/2014 | Parihar | |
| 2014/0243799 A1 | 8/2014 | Parihar | |
| 2014/0243800 A1 | 8/2014 | Parihar | |
| 2014/0277018 A1 | 9/2014 | Parihar | |
| 2014/0378953 A1 | 12/2014 | Coe et al. | |
| 2015/0088191 A1 | 3/2015 | Coe et al. | |
| 2016/0007979 A1* | 1/2016 | Bhagat | A61B 17/3403 604/175 |

FOREIGN PATENT DOCUMENTS

| | | |
|---|---|---|
| JP | 2005-261734 A | 9/2005 |
| JP | 2008-518716 A | 6/2008 |
| WO | WO-94/04067 A1 | 3/1994 |
| WO | 2008/015666 A2 | 2/2008 |
| WO | 2010/060436 A1 | 6/2010 |
| WO | 2010/081482 A1 | 7/2010 |
| WO | 2010/111319 A1 | 9/2010 |
| WO | 2010/114634 A1 | 10/2010 |
| WO | 2011/044353 A1 | 4/2011 |
| WO | 2011/081702 A1 | 7/2011 |
| WO | 2011/089565 A1 | 7/2011 |
| WO | 2012/035524 A2 | 3/2012 |
| WO | 2012/040183 A1 | 3/2012 |
| WO | 2012/112622 A2 | 8/2012 |
| WO | 2012/126967 A2 | 9/2012 |
| WO | 2013/007764 A2 | 1/2013 |
| WO | 2013/048963 A2 | 4/2013 |
| WO | 2014/052177 A1 | 4/2014 |

OTHER PUBLICATIONS

[No Author Listed] "A Single Solution for Any Port," Stryker Corporation. Product Brochure; 2009, 2 pages.
International Search Report dated Mar. 21, 2011; International Application No. PCT/US2010/051812 (7 pages).
International Preliminary Report dated Apr. 19, 2012; International Application No. PCT/US2010/051812; (10 pages).
International Search Report dated Mar. 2, 2012; International Application No. PCT/US2011/050198 (7 pages).
International Preliminary Report dated Mar. 14, 2013; International Application No. PCT/US2011/050198 (10 pages).
International Search Report dated Dec. 12, 2011; International Application No. PCT/US2011/052327 (5 pages).
International Preliminary Report dated Apr. 4, 2013; International Application No. PCT/US2011/052327 (9 pages).
International Search Report dated Apr. 3, 2013; International Application No. PCT/US2012/056900 (3 pages).
International Preliminary Report dated Apr. 10, 2014; International Application No. PCT/US2012/056900 (8 pages).
International Search Report dated Dec. 20, 2013; International Application No. PCT/US2013/060803 (3 pages).
International Preliminary Report dated Apr. 9, 2015; International Application No. PCT/US2013/060803 (9 pages).
International Search Report dated May 28, 2014; International Application No. PCT/US2014/015738 (4 pages).
International Preliminary Report on Patentability dated Sep. 11, 2015; International Application No. PCT/US2014/015738 (12 pages).
US Application as filed on Oct. 9, 2009 for U.S. Appl. No. 12/576,529 (18 pages).
International Search Report and Written Opinion dated Oct. 31, 2016; International Application No. PCT/US2016/052033 (12 pages).

* cited by examiner

POSITIONING DEVICE FOR USE WITH SURGICAL INSTRUMENTS

FIELD

This disclosure relates generally to surgical instruments and, more particularly, to devices and methods for positioning a surgical instrument that is percutaneously inserted into a patient.

BACKGROUND

Surgical procedures are used to treat and cure a wide range of diseases, conditions, and injuries. Surgery often requires access to internal tissue through open or minimally invasive surgical procedures. The term "minimally invasive" refers to a wide range of surgical procedures including laparoscopic, arthroscopic, endoscopic, natural orifice intraluminal, and natural orifice transluminal procedures. Minimally invasive surgery can have numerous advantages compared to traditional open surgical procedures, including reduced trauma, faster recovery, reduced risk of infection, and reduced scarring. During some minimally invasive procedures, trocars can be used to provide a port through which endoscopic surgical instruments are passed into a patient's body.

Development in minimally invasive surgery has resulted in increasingly complex procedures that require multiple instruments and precise manipulations within the body. Because of the limited access space afforded by a trocar and the relatively larger wound size associated therewith, one solution has been the use of percutaneous surgical instruments inserted directly into a body cavity and used to supplement instruments introduced through one or more trocars. For example, procedures have been developed that involve additional percutaneous instruments to aid in retracting organs and structures. In other procedures, one or more percutaneous instruments having removable end effectors are utilized in combination with a trocar that can accommodate the passage of various end effectors. Inserting surgical instruments percutaneously, i.e., passing directly through tissue without an access device, can further reduce trauma and scarring to the patient by reducing the size of the wound created.

The increasing use of percutaneously inserted surgical instruments is not without challenges, however. For example, using an increasing number of these instruments can require an increased number of operators to handle and position the devices during a procedure. A surgeon or other user cannot, by way of further example, position an instrument as desired and then leave the instrument unattended while they attend to operating another, or several other, instruments.

Accordingly, there is a need for devices and methods that allow a user to selectively maintain a percutaneous surgical instrument in a desired position and/or orientation such that the user can free their hands for other tasks.

BRIEF SUMMARY

The present disclosure generally provides devices and methods for positioning and maintaining percutaneously inserted surgical instruments in fixed orientations without the need for an operator to maintain the orientation of the surgical instrument by hand. For example, in some embodiments the devices described herein can generally include a base, a shuttle, and a locking mechanism. The base can be placed on the patient, and the operator can place a surgical instrument within a lumen of the shuttle to allow for movement relative to the base. Moreover, the operator can adjust the angle of approach of the surgical instrument within the shuttle relative to the base and percutaneously insert a working end of the surgical instrument into the patient. In fact, the operator can move the instrument across six degrees of freedom. When the operator is satisfied with the working location of the surgical instrument, the operator can actuate the locking mechanism to restrict movement of the instrument across any or all degrees of freedom.

In one aspect, a surgical instrument positioning device can include a base configured to be placed against tissue such that the base does not move relative thereto, as well as a shuttle coupled to the base and including a lumen configured to receive an elongate shaft of a surgical instrument. The lumen can translate in at least two directions relative to the base and an orientation of the lumen relative to the base can be polyaxially adjusted. The device can further include a locking mechanism that, upon actuation, prevents both translational movement of the lumen relative to the base and polyaxial adjustment of the orientation of the lumen relative to the base.

The devices and methods described herein can include a variety of additional features or modifications, all of which are considered within the scope of the present invention. For example, in some embodiments, the base can have an adhesive disposed on a surface thereof that is placed against tissue to aid in preventing relative motion between the device and a patient. The base can also have any desired dimensions and/or rigidity. In certain embodiments, the length and width of the base can be greater than a thickness thereof.

The lumen can be capable of translation in at least two directions relative to the base. For example, the lumen can be capable of translating in a direction parallel to a length of the base and a direction parallel to a width of the base. Moreover, the locking mechanism can be configured to prevent translational or rotational movement of a surgical instrument received by the lumen relative to the lumen upon actuation. In certain embodiments, the locking mechanism can be configured to be actuated by a single motion to lock a surgical instrument received by the lumen across six degrees of freedom. Such a locking mechanism can be, in certain embodiments, a single cam lock.

In another aspect, a surgical instrument positioning device can include a base configured to be placed against tissue such that the base does not move relative thereto, as well as a socket coupled to the base and capable of translating in at least two directions relative to the base. The device can further include a ball configured to be seated within the socket with the ball including a lumen formed in it that is configured to receive an elongate shaft of a surgical instrument. The device can also include a locking mechanism that, upon actuation, prevents both movement of the ball within the socket and translation of the socket relative to the base.

In some embodiments, the base can include an adhesive disposed on a surface thereof that is placed against tissue to aid in preventing relative movement between the device and a patient's body. As noted above, the base can have any of a variety of shapes and sizes. In certain embodiments, a length and a width of the base can be greater than a thickness thereof.

The socket coupled to the base can be capable of translating in at least two directions relative thereto. In some embodiments, the socket can be capable of translating in a first direction that is parallel to a length of the base and a second direction that is parallel to a width of the base.

Beyond preventing movement of the ball within the socket and translation of the socket relative to the base, in some embodiments the locking mechanism can be further configured to prevent translational or rotational movement of a surgical instrument received by the ball relative to the ball upon actuation. Moreover, the locking mechanism can be configured to be actuated by a single motion to lock a surgical instrument received by the ball across six degrees of freedom. As mentioned above, in certain embodiments, the locking mechanism can be a single cam lock.

In yet another aspect, a method for positioning a surgical instrument can include placing a base of a positioning device against tissue and passing a surgical instrument through a lumen formed in the positioning device. The method can further include translating the surgical instrument in at least two dimensions relative to the base and polyaxially adjusting an orientation of the surgical instrument relative to the base. The method can also include locking a position and orientation of the surgical instrument relative to the base.

In some embodiments, placing the base of the positioning device against tissue can include adhering a surface of the base to the tissue. In other embodiments, translating the surgical instrument in at least two dimensions relative to the base can include moving the surgical instrument along an axis parallel to a width of the base and moving the surgical instrument along an axis parallel to a length of the base.

In certain embodiments, locking a position and orientation of the surgical instrument relative to the base can include locking the instrument across six degrees of freedom. Moreover, in some embodiments, locking a position and orientation of the surgical instrument relative to the base can include operating an actuator with a single actuating movement to lock the surgical instrument across six degrees of freedom.

The various steps of the method described above can be performed before or after an instrument is inserted into a patient's body. Accordingly, in some embodiments, the method can further include passing the surgical instrument through the tissue positioned against the base.

Any of the features or variations described above can be applied to any particular aspect or embodiment of the invention in a number of different combinations. The absence of explicit recitation of any particular combination is due solely to the avoidance of repetition in this summary.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Figure 1:
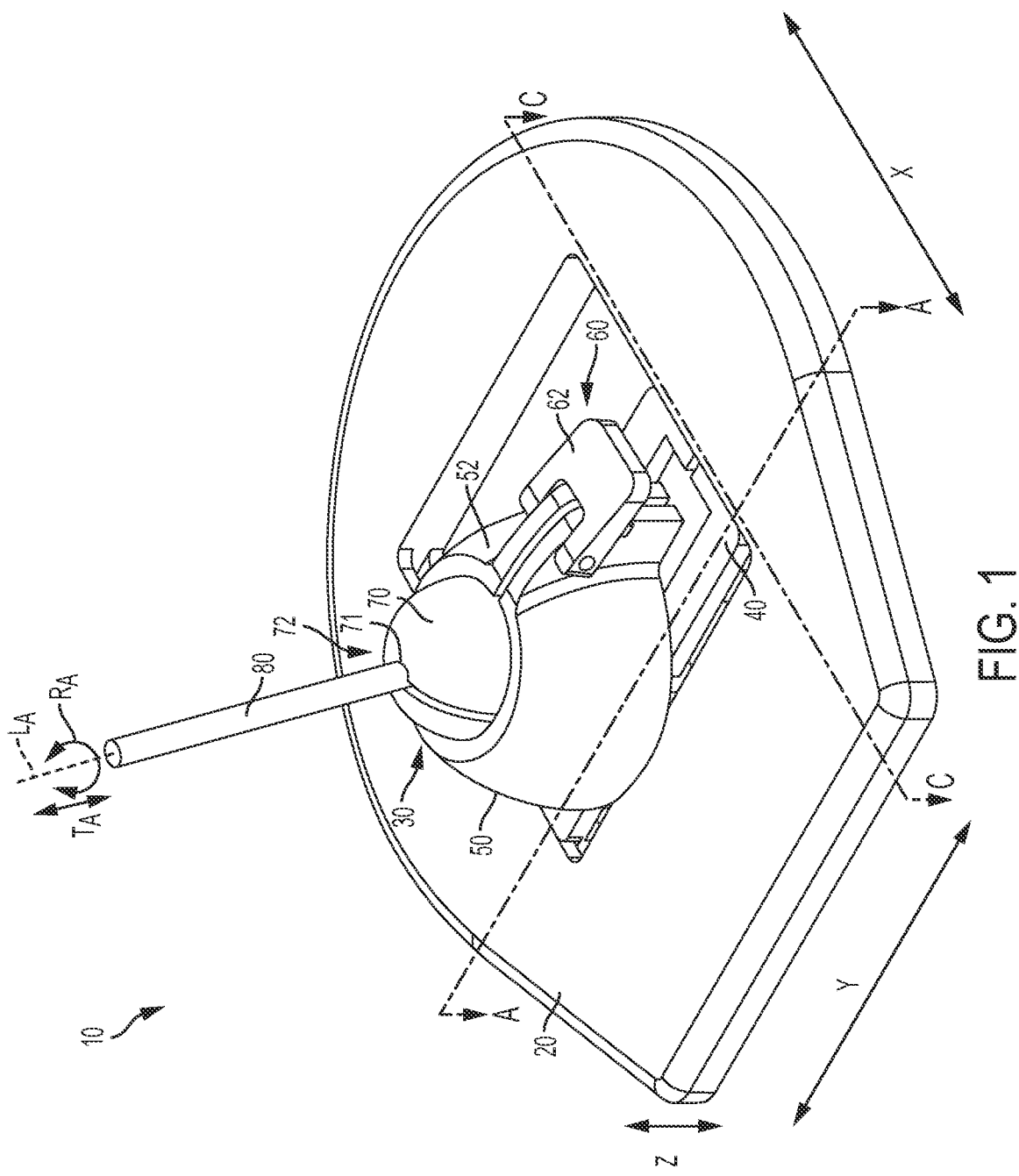
FIG. 1 is a perspective view of one embodiment of a surgical instrument positioning device in an unlocked configuration.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The terms "proximal" and "distal" are used herein with reference to a clinician manipulating the handle portion of the surgical instrument, with the term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute. Still further, a person skilled in the art will recognize that a number of different terms can be used interchangeably while still being understood by the skilled person, for example, "instrument" and "tool."

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Further, sizes and shapes of the devices, and the components thereof, can depend at least on the anatomy of the subject in which the devices will be used, the size and shape of components with which the devices will be used, and the methods and procedures in which the devices will be used.

The present disclosure generally relates to positioning devices for selectively holding a surgical instrument in a fixed position and/or orientation relative to a patient. One advantage of such positioning devices can be allowing a surgeon to maintain certain surgical instruments in fixed orientations and freeing the surgeon to use both hands to proceed with other portions of the procedure. Another advantage of certain embodiments of the positioning devices described herein is that a surgical instrument can be manipulated in six degrees of freedom relative to the positioning device, namely, forward and backward, up and down, and left and right in the perpendicular axes, combined with rotation about three perpendicular axes, often referred to as pitch, roll, and yaw. Moreover, in some embodiments a single locking member can fix the orientation of the surgical instrument in all degrees of freedom.

Figure 2:
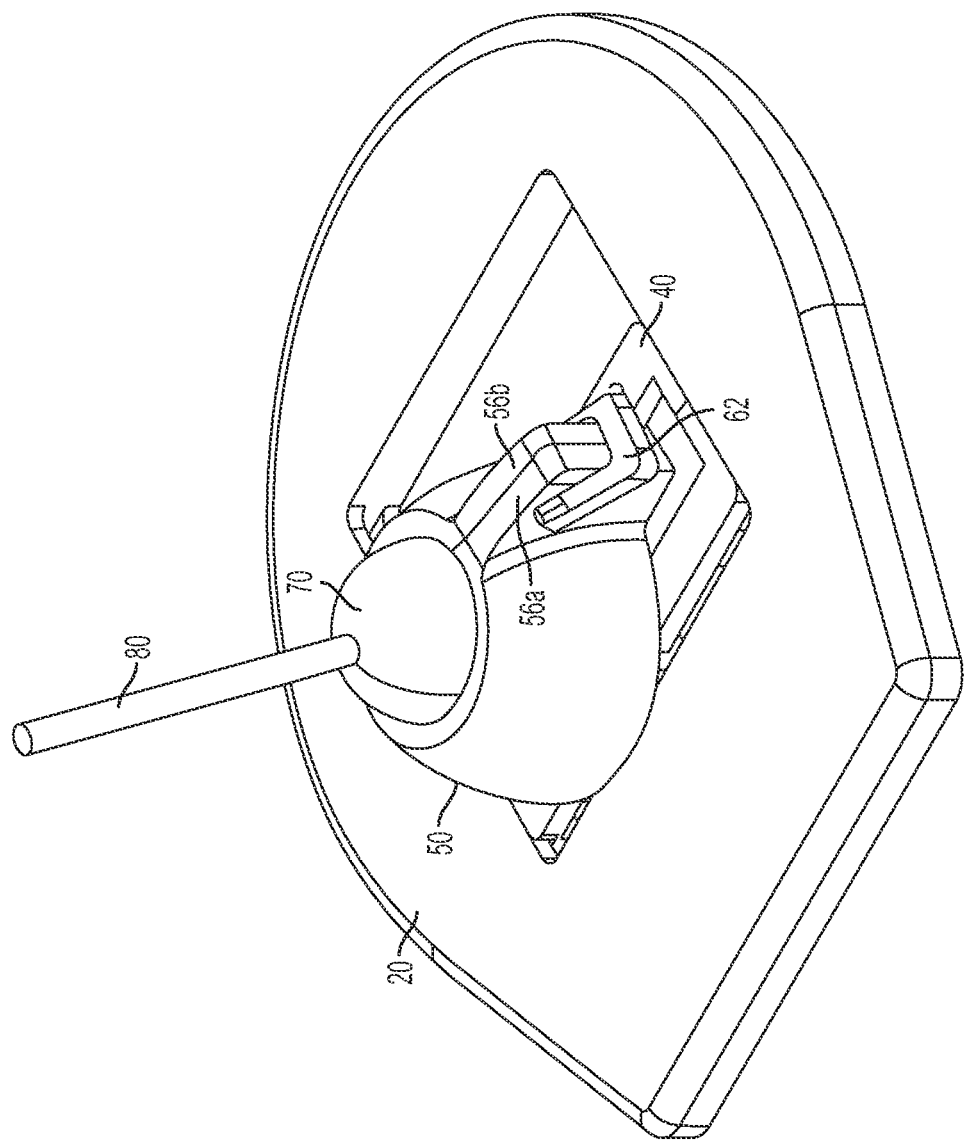
FIG. 2 is a perspective view of the surgical instrument positioning device of FIG. 1 in a locked configuration.
Figure 3:
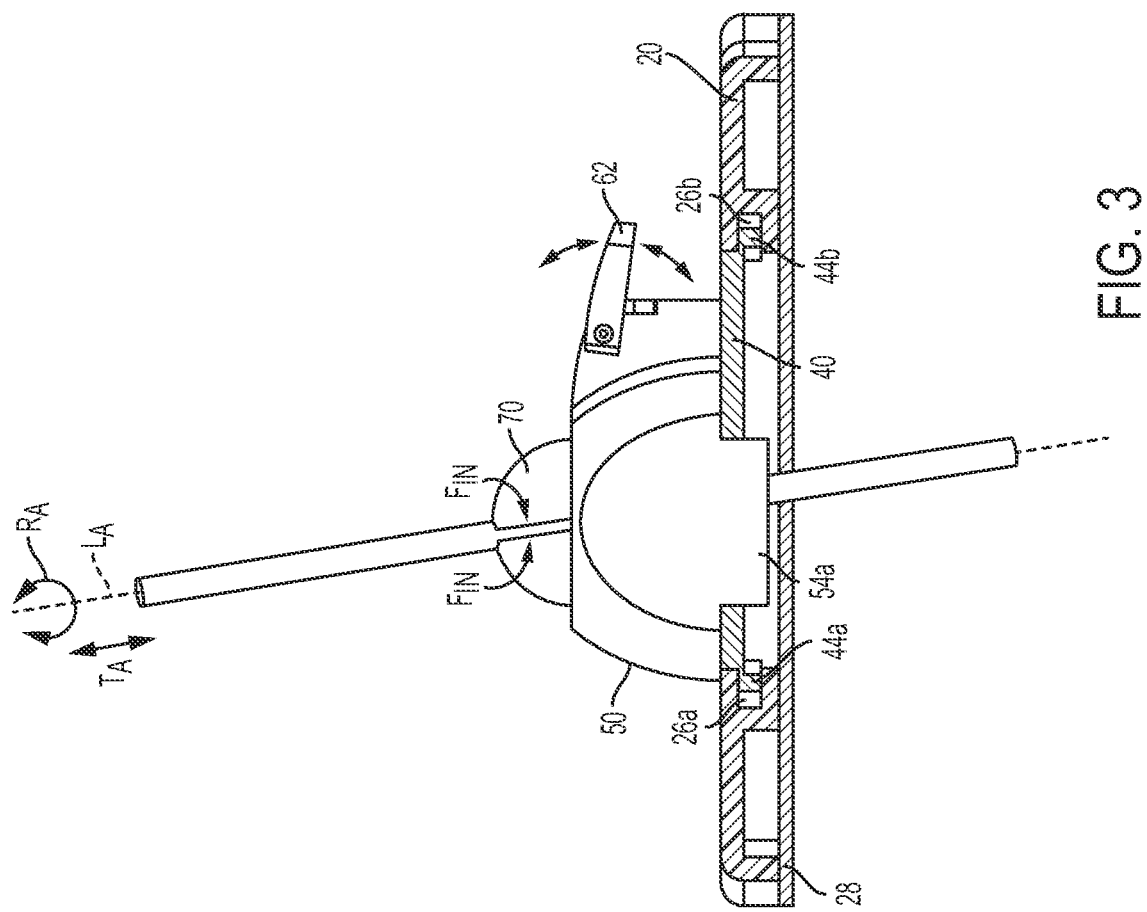
FIG. 3 is a cross-sectional view of the surgical instrument positioning device of FIG. 1 taken along the line A-A.

As shown in FIGS. 1-3, a positioning device 10 can include a base 20, a shuttle 30, and a locking mechanism 60. The shuttle 30 can include a lumen 72 that can be sized to receive a surgical instrument 80, and can be further configured to allow an operator to manipulate the surgical instrument 80 in six degrees of freedom (referenced above) relative to the base 20 when in an unlocked configuration, as shown in FIG. 1. Conversely, when in a locked configuration (as shown in FIG. 2), the surgical instrument 80 can be prevented from moving in all six degrees of freedom.

Figure 4:
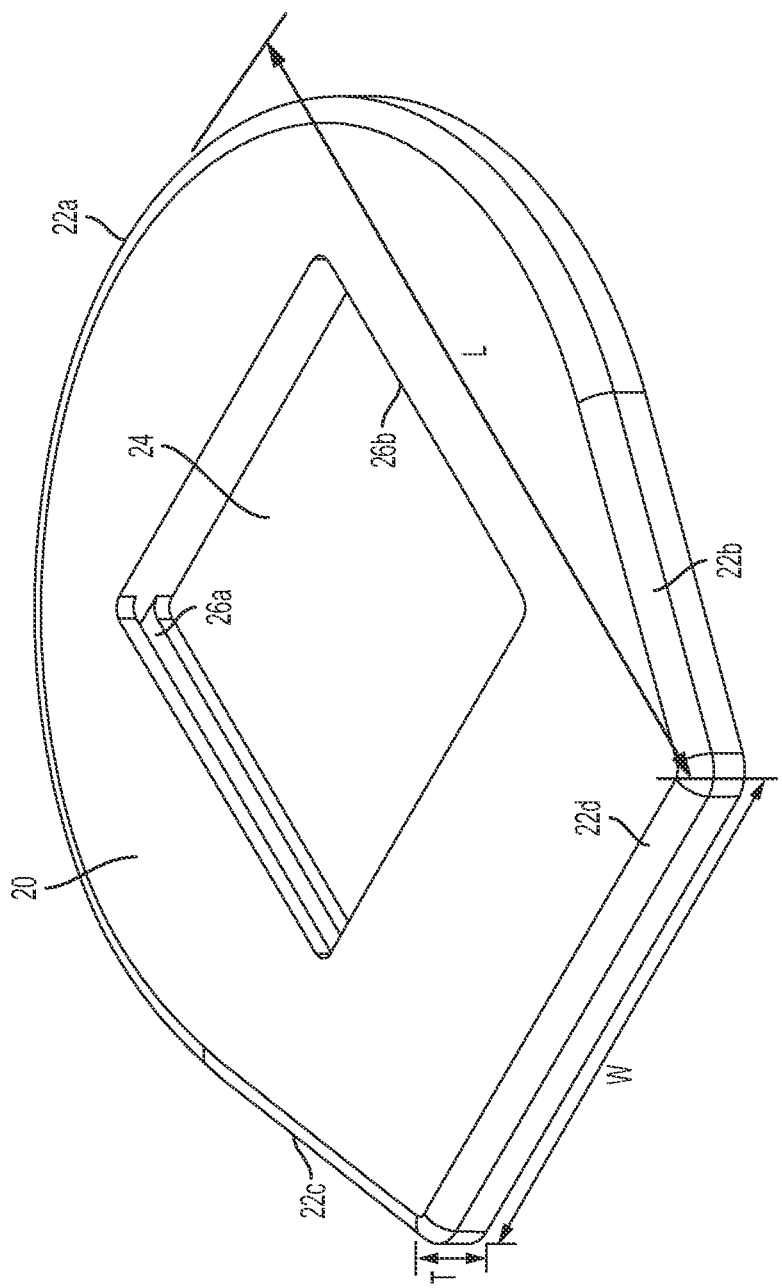
FIG. 4 is a perspective view of a base of the surgical instrument positioning device of FIG. 1.

The shuttle 30 can include a slider 40 and a pivot joint 50 that, together, provide for translation in a plane (i.e., translation in two directions) parallel to a top surface of the base 20. For example, the slider 40 can slide along the X travel axis, as shown in FIG. 1, which is parallel to the length L of the base 20, as seen in FIG. 4. In addition, the pivot joint 50 can move along the slider 40 to allow for movement along the Y travel axis, which is parallel to the width W of the base 20, as also shown in FIG. 4. The pivot joint 50 can further include a socket 52 and a ball 70 which can provide an additional four degrees of freedom. The lumen 72 can be located within the ball 70 such that a surgical instrument 80 can be slidingly located therein to allow for rotational and/or translational movement along a longitudinal axis $L_A$ (as shown by arrows $R_A$ and $T_A$, respectively). Further, the ball 70 can be located within the socket 52 to permit polyaxial movement of the instrument 80 relative to the pivot joint 50.

The locking mechanism 60 can be utilized to selectively inhibit movement of the surgical instrument 80 in any or all degrees of freedom. In some embodiments, the locking mechanism 60 can include a locking tab 62 that can be used to transition between locked and unlocked configurations. In an unlocked configuration, the locking mechanism 60 can permit movement of the tool 80 in at least six degrees of freedom and, in a locked configuration, the locking mechanism 60 can restrict all movement of the tool relative to the device 10. Movement of the locking tab 62 can transition the locking mechanism 60 from the unlocked orientation to the locked orientation. In the illustrated embodiment, movement of the locking tab 62 causes the slider 40 to be locked relative to the base 20 by compressing the slider 40 to create an interference fit between the slider and the base. Similarly, when the pivot joint 50 is compressed there is interference between the pivot joint 50 and the slider 40, thereby preventing relative movement between these components. The pivot joint 50 can further be compressed about the ball 70 such that an interference fit is created, thereby restricting polyaxial movement of the ball 70 relative to the socket 52. Still further, compression of the ball 70 can create an interference fit between inner walls 71 of the ball 70 that define the lumen 72 and the surgical tool 80, thereby preventing any translational or rotational movement of the surgical tool 80 relative to the lumen 72 of the ball. In some embodiments, movement of the locking tab 62 can be the only required action to prevent movement across all degrees of freedom of the surgical instrument 80. Alternatively, each degree of freedom, or combinations thereof, can be restricted individually with additional locking tabs 62 or other mechanisms known in the art.

FIG. 4 illustrates one exemplary embodiment of a base 20 of the positioning device 10. The base 20 can have any shape and size depending, at least in part, on the shape and size of the other components of the positioning device 10, the shape and size of any other instruments or tools with which it is used, and the type of procedure being performed. In the illustrated embodiment, the base is substantially elongate and generally flat with a length L and width W of the base 20 being larger than its thickness T. Alternatively, the base can be curved in certain portions instead of flat to more easily mimic portions of a patient's anatomy. In the illustrated embodiment, the base 20 has a circular or elliptical shape with a single flat side, although many other shapes (e.g., rectangular, fully circular or elliptical, pentagonal, etc.) or combinations thereof can be used. As shown, the base 20 of FIG. 4 has four sides 22a, 22b, 22c, and 22, with the first side 22a having a generally curved horseshoe shape, the second and third sides 22b, 22c extending tangentially from the ends of the first side 22a, and the fourth side 22d extending from the other ends of the second and third sides 22b, 22c.

The base 20 can further include a central opening 24 configured to receive the shuttle 30. The central opening 24 can be any suitable shape that permits relative movement between the shuttle 30 and the base 20. For example, the central opening 24 can have a rectangular shape, a square shape, a parallelogram shape, a circular shape, an elliptical shape, or any other shape that allows for movement of the shuttle 30 relative to the base 20. In the illustrated embodiment, the central opening 24 is generally rectangular. As shown in FIG. 3, the central opening 24 can have two opposed parallel mating features 26a, 26b. The mating features 26a, 26b can be any structures that provide an interface for the shuttle 30 to move in at least a first degree of freedom, for example along the travel axis X of FIG. 1. The mating features 26a, 26b, as shown in FIGS. 3 and 4, can be channels formed into the base 20 to allow for mating tongue elements 44a, 44b of the slider 40 (see FIG. 6) to move within the central opening 24 of the base 20. In other embodiments, this arrangement can be reversed such that the mating features 26a, 26b can be tongue elements configured to fit within mating grooves formed on the slider 40 to allow for relative sliding movement. Any other mating features that facilitate movement between structures can be incorporated into the base 20 and slider 40 without departing from the spirit of the present disclosure.

While the size and shape can vary at least depending on the factors described above, in some exemplary embodiments, the length L of the base 20 can be approximately in the range of about 15 millimeters to about 25 millimeters, the width W can be approximately in the range of about 15 millimeters to about 25 millimeters, and the thickness T can be approximately in the range of about 5 millimeters to about 15 millimeters. In the illustrated embodiment the length is approximately about 25 millimeters, the width has a smallest dimension of about 15 millimeters and a largest dimension of about 25 millimeters, and the thickness is about 7 millimeters. Further, in some embodiments the base 20 can be made of materials that allow it to be rigid, thereby providing additional support to any surgical instrument 80 inserted within a patient, while in other embodiments, the base 20 can be made of more flexible materials. Some non-limiting examples of the types of materials that can be used to make the base 20 include various metals and polymers such as polycarbonate, nylon, ULTEM, liquid crystal polymer, surgical grade stainless steel, aluminum, or titanium.

In some embodiments, the base 20 can include an adhesive 28 disposed on a lower, body-facing surface of the base 20, as shown in FIG. 3. The adhesive 28 can provide for improved stability and resistance to movement between the device 10 and the patient. The adhesive 28 can be any of a number of adhesives having various compositions and strengths. Exemplary adhesives can include acrylate, methacrylates, or epoxy dicrylates. The adhesive 28 can cover the entire lower surface of base 20 or, alternatively, the adhesive 28 can cover only a portion of the lower surface of the base 20. Although illustrated in FIG. 3, the adhesive 28 is not required for the device 10 to be effective during a surgical procedure and can be omitted. Moreover, in some embodiments, alternative materials (e.g., tacky or high friction materials) and/or surface features (e.g., bumps, ridges, teeth, etc.) can be used in place of, or in addition to, an adhesive to aid in securing the base 20 relative to a patient.

Figure 5:
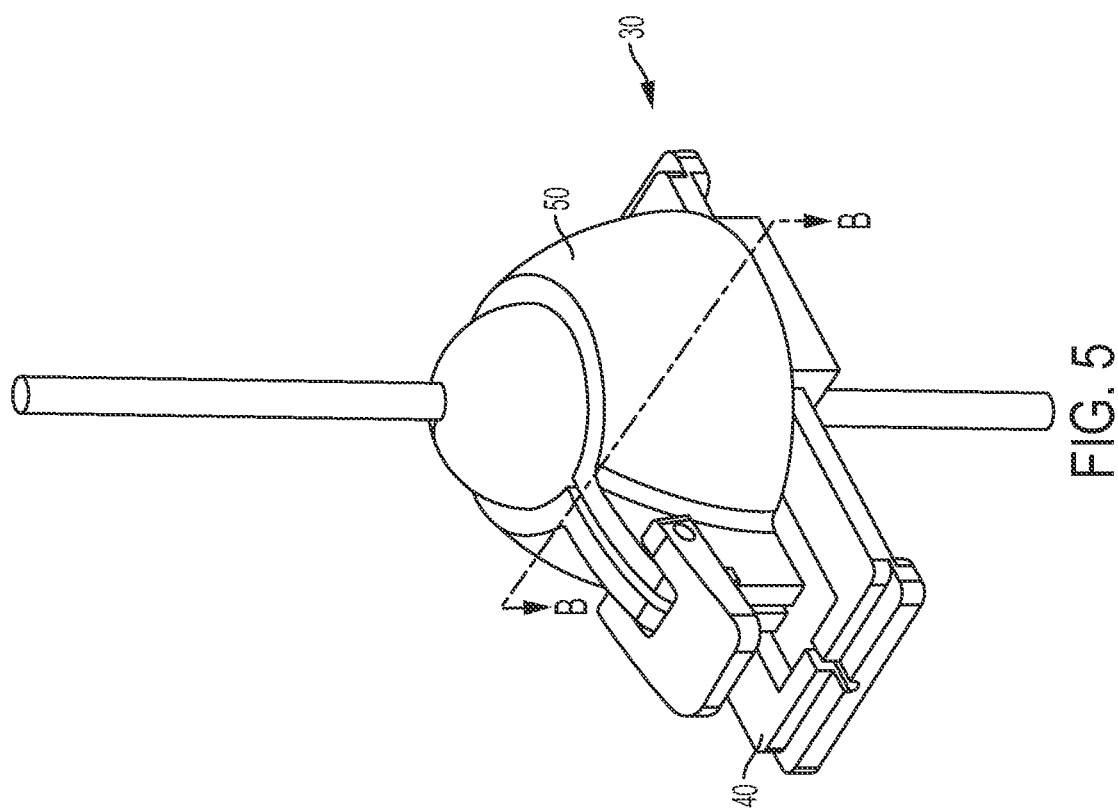
FIG. 5 is a perspective view of a shuttle of the surgical instrument positioning device of FIG. 1.

FIG. 5 shows a detailed view of one embodiment of a shuttle 30. The shuttle 30 can be designed to allow for translational movement of the surgical tool 80, housed in the lumen 72, in a plane that is parallel to a top surface of the base 20 in at least two degrees of freedom. The at least two degrees of freedom provided by the shuttle 30 to the tool 80 can be, for example, along a first travel axis X that can be parallel to the length L of the base 20 and along a second travel axis Y that can be parallel to the width W of the base 20, as shown in FIG. 1. The shuttle 30 can include a slider 40 and a pivot joint 50. The slider 40 and the pivot joint 50 can be two separate assemblies that are able to translate relative to each other. This relative translation, in combination with translation of the slider 40 relative the base 20, can enable the compound movement provided by the shuttle 30 to the surgical instrument 80.

Figure 6:
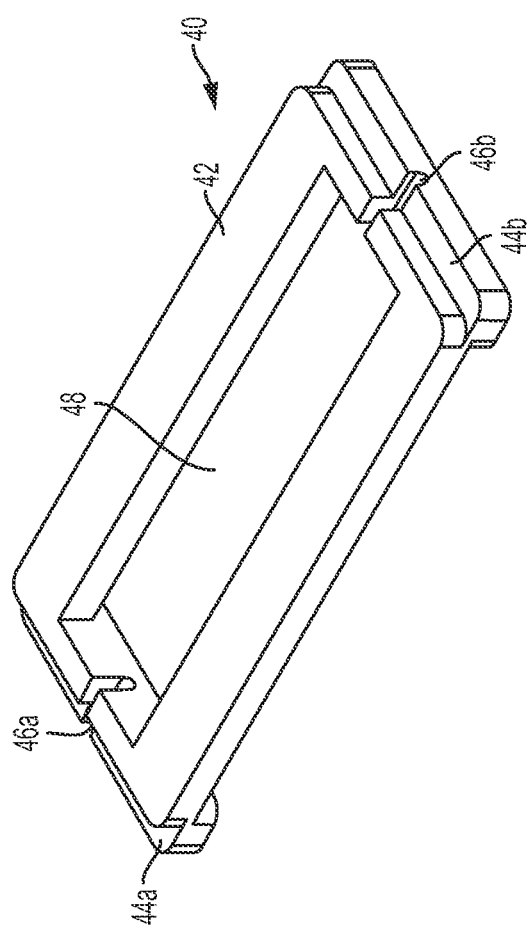
FIG. 6 is a perspective view of a slider of the shuttle of FIG. 5.

In the illustrated embodiment of FIG. 6, the slider 40 is generally rectangular and sized to be slidingly received within the central opening 24 of the base 20 to allow for linear movement of the shuttle 30 along the travel axis X. The slider 40 can include mating features 44a, 44b for mating with corresponding mating features 26a, 26b of the base 20, as shown in FIG. 3. The mating features 44a, 44b can, for example, generally extend along a width of the body 42 from a lower surface thereof such that the mating features 44a, 44b extend past the edge of the body 42 of the slider 40 along a length thereof. The mating features 44a, 44b can, for example, be tongues sized to be slidable within the grooves 26a, 26b of the base 20. As noted above, in other embodiments, this arrangement can be reversed such that the mating features 44a, 44b can be grooves sized to receive corresponding mating features 26a, 26b of the base 20. In still other embodiments, the base 20 and the slider 40 can be mated to one another using any known configuration that allows for relative movement between the two components.

In some embodiments, the slider 40 can include features to allow the slider 40 to be selectively locked relative to the base 20 when the locking mechanism 60 is actuated. In the illustrated embodiment, for example, the slider can include two U-shaped slots 46a, 46b which can create a pivot joint around which the slider 40 can flex. The U-shaped slots 46a, 46b can extend through a portion of the body 42 and the mating features 44a, 44b. The U-shaped slots 46a, 46b can be axially aligned, or alternatively can be located at different positions along the width of the slider 40. The body 42 of the slider 40 can also include a central opening 48 that can increase the flexibility of the slider 40 and reduce the force required to flex the slider about the U-shaped slots 46a, 46b. Flexing of the slider 40 about the U-shaped slots 46a, 46b can be utilized to produce an interference fit between the base 20 and the slider when the locking mechanism 60 is actuated, as discussed further below.

Figure 7:
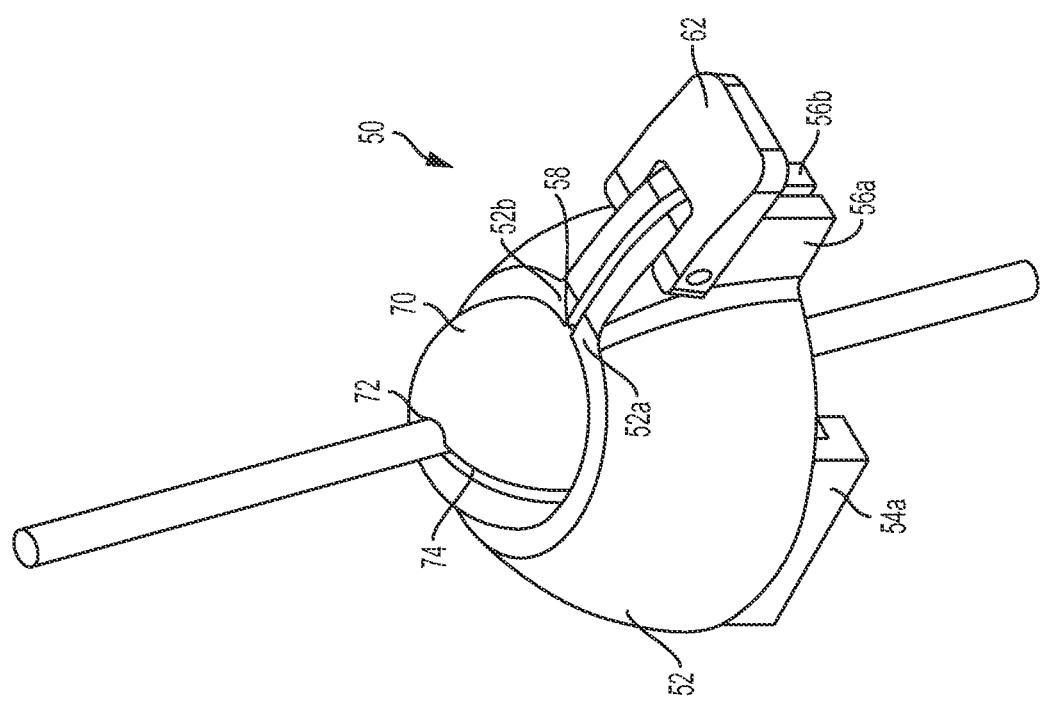
FIG. 7 is a perspective view of a pivot joint of the shuttle of FIG. 5.
Figure 8:
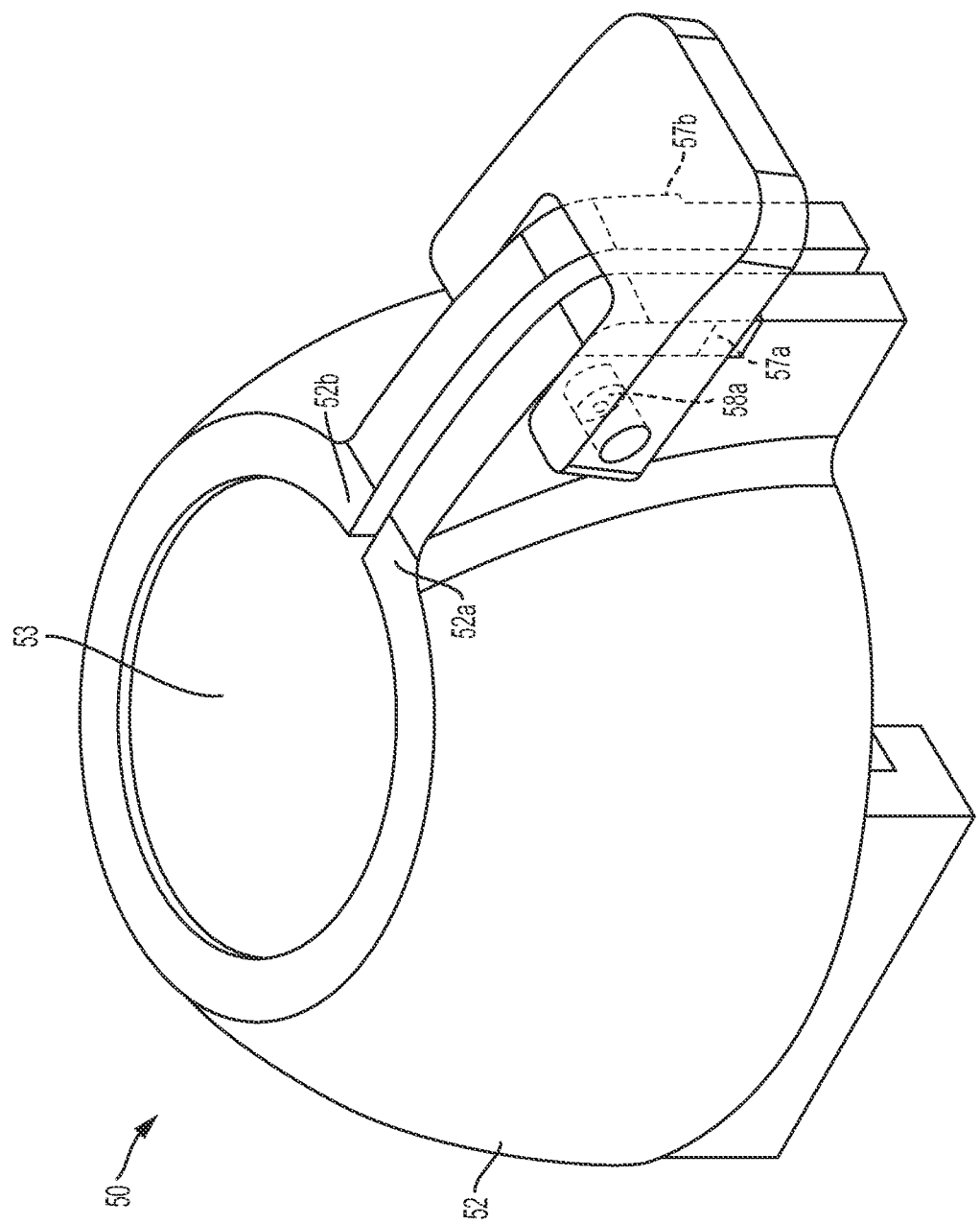
FIG. 8 is a perspective view of a socket of the pivot joint of FIG. 5.
Figure 9:
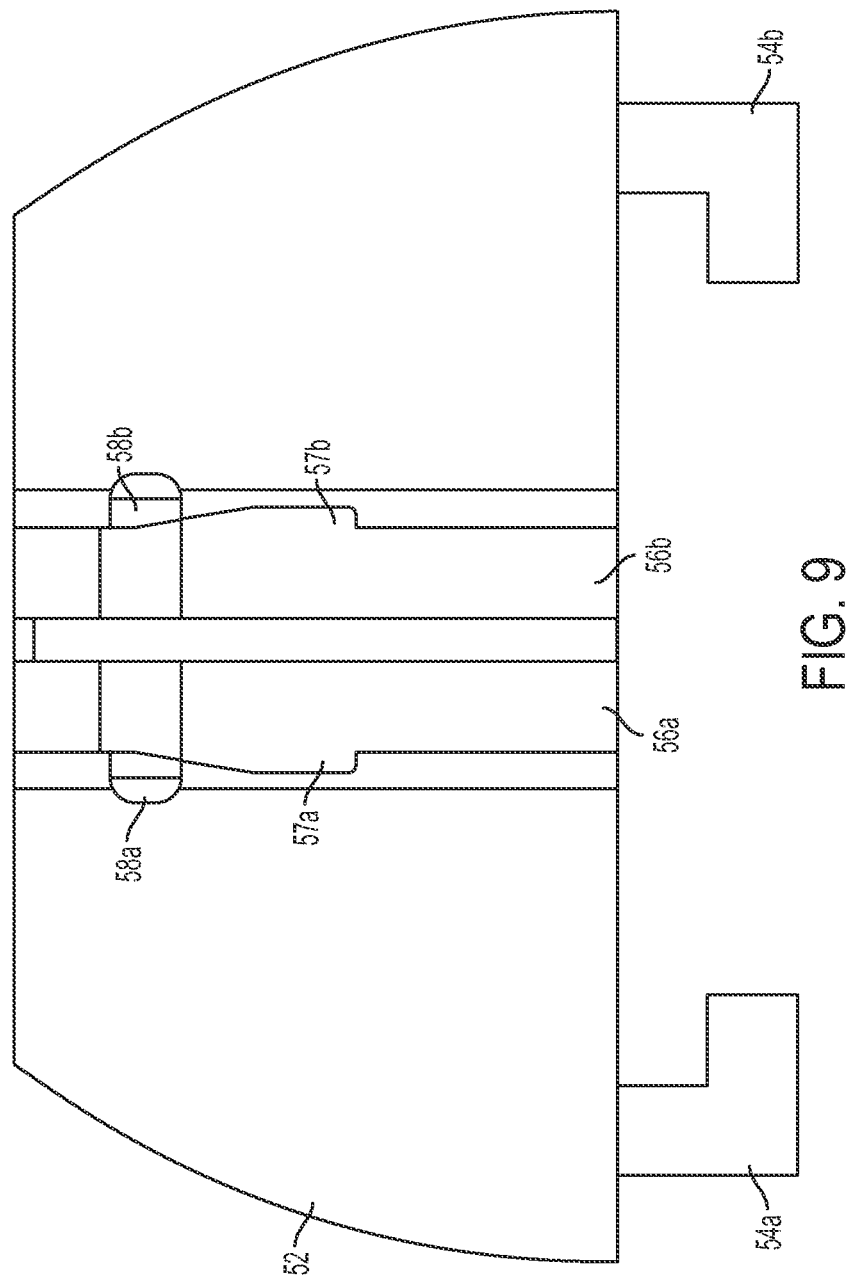
FIG. 9 is a front view of the pivot joint of FIG. 5.
Figure 10:
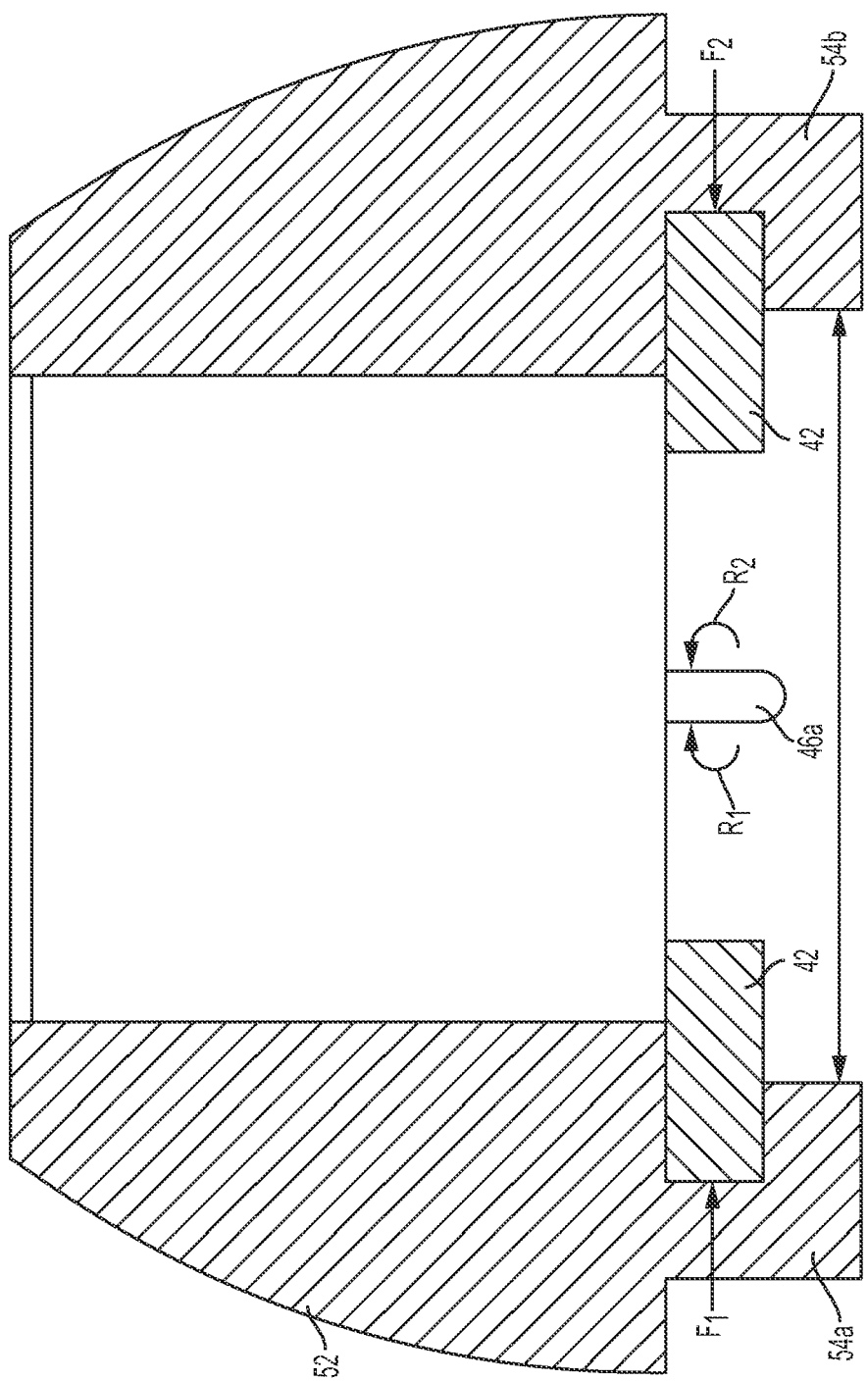
FIG. 10 is a cross-sectional view of the shuttle of FIG. 5 taken along the line B-B.

FIGS. 7-10 illustrate the pivot joint 50 of the shuttle 30. The pivot joint 50 can include a generally dome shaped portion 52 having at least two mating features 54a, 54b disposed on a lower surface, as shown in FIG. 9. The mating features 54a, 54b can be, for example, tracks that extend from a lower surface of the pivot joint 50. The tracks 54a, 54b can have an L-shape, as shown in FIGS. 9 and 10, and can be sized to slidingly receive respective side portions of the slider body 42. The two mating tracks 54a, 54b can allow for translating (e.g., sliding) movement of the pivot joint 50 relative to the slider 40 along the travel axis Y of the base 20.

In some embodiments, the dome portion 52 can include a spherical shaped socket 53, which can be sized to receive a ball 70. In addition, the pivot joint 50 can include a slot 58 extending from a top of the dome shaped portion 52 to a lower surface thereof. The two ends 52a, 52b of the pivot joint 50 that define the slot 58 can be configured to contract toward one another, thereby creating an interference fit between the dome shaped portion 52 and the ball 70 when the device 10 is moved to a locked configuration. Further, when the two ends 52a, 52b of the pivot joint are compressed toward or against one another, the mating tracks 54a, 54b can compress against the slider 40 to create an interference fit between the pivot joint 50 and the slider.

The ball 70 can be housed within the socket 53 of the dome shaped portion 52 of the pivot joint 50. The ball 70 can include a through-hole 72, or lumen, which can receive a surgical tool 80 to allow for polyaxial movement of the tool relative to the base 20. When the ball 70 is housed within the pivot joint 50, the ball can move polyaxially and provide three rotational degrees of freedom, including pitch, roll, and yaw. The surgical tool 80 can additionally rotate (as shown by the arrow $R_A$ in FIG. 3) and translate (as shown by the arrow $T_A$ in FIG. 3) within the through-hole 72 to allow for movement about the longitudinal axis $L_A$ of the through-hole 72. The ball 70 can further have a slot 74 which can allow the ball 70 to be compressed against the instrument 80 and thereby retain it in a fixed position relative to the ball when the locking mechanism 60 is actuated.

The pivot joint 50 can further include two lock support members 56a, 56b extending radially from the dome shaped portion 52 of the pivot joint 50. The lock support members 56a, 56b can be located on the two ends 52a, 52b, respectively, of the dome shaped portion 52 that define the slot 58, as shown in FIGS. 8 and 9. The lock support member 56a can further include a pivot pin 58a. The pin 58a can be sized to be rotatably received in the locking tab 62. A corresponding pivot pin 58b can be axially aligned and located on the other lock support member 56b to rotatably support the locking tab 62. In some embodiments, however, the two pivot pins 58a, 58b can be replaced by a single pin that extends through the two lock support members 58a, 58b and across the slot 58. The lock support members 56a, 56b can additionally include cam surfaces 57a, 57b configured to interface with the locking tab 62. As shown in FIG. 9, the cam surfaces 57a, 57b can have a ramp-like profile, in which a thickness of the cam surfaces 57a, 57b increases as they extend along the lock support members 56a, 56b from a proximal (upper) end of the device 10 to a distal (lower) end of the device. The locking tab 62 can ride along the cam surfaces 57a, 57b to lock and unlock the device 10, as discussed further below. In other embodiments, the orientation of the cam surfaces 57a, 57b can be reversed, effectively reversing the direction the locking tab 62 can be moved to actuate the locking mechanism 60.

In the illustrated embodiment of FIGS. 7 and 8, the locking tab 62 is a cam lock that pivots about the pivot pins 58a, 58b. As shown, the locking tab 62 can have a cutout sized to receive the lock support members 56a, 56b. The cutout of the locking tab 62 can have a fixed width. As a result, when the locking tab 62 is rotated from an unlocked position, as shown in FIG. 1, to a locked position, as shown in FIG. 2, the locking tab 62 can abut against the cam surfaces 57a, 57b and cause the lock support members 56a, 56b to compress toward one another. The compression of the lock support members 56a, 56b toward one another can restrict movement of the surgical instrument 80 relative to the device 10, as described below. The locking tab 62 and cam surfaces 57a, 57b are just one example of a configuration that can be used to lock the device and restrict movement of a surgical instrument. Any other known configuration can be employed as well, including, by way of a non-limiting example, a toggle tab extending through the lock support members 56a, 56b (e.g., similar to a bicycle wheel quick release attachment).

As mentioned above, when the locking tab 62 is rotated downward from the unlocked position of FIG. 1, to the locked position of FIG. 2, all six degrees of freedom can be locked with a single motion. The locking tab 62 can ride along the cam surfaces 57a, 57b and, because the cutout of the locking tab 62 has a fixed width, the two lock support members 56a, 56b can be pushed together as the locking tab 62 is pushed downward toward the increased thickness portions of the cam surfaces. The movement of the two lock support members 56a, 56b towards one another can cause the dome shaped portion 52 of the pivot joint 50 to compress about the ball 70. This compressive force can create an interference fit that can restrict the polyaxial movement of the ball 70 within the socket 53 of the pivot joint 50. The compression of the ball 70 can reduce the size of the slot 74 formed therein (as shown by arrows $F_{IN}$ shown in FIG. 3), which can allow the ball to securely grasp the surgical instrument 80, as shown in FIG. 2. The surgical tool 80 can thereby be prevented from rotating (as shown by arrow $R_A$ in FIG. 3) and/or translating (as shown by arrow $T_A$ in FIG. 3) relative to the ball 70. The compression of the lock support members 56a, 56b can also result in the compression of the mating tracks 54a, 54b on the bottom of the pivot joint 50. The compression can cause forces $F_1$, $F_2$ (see FIG. 10) to be exerted on the body 42 of the slider 40, thereby creating interference that restricts translational (e.g., sliding) movement of the pivot joint 50 along the slider 40 by increasing the frictional forces between the tracks 54a, 54b and the body portion 42 of the slider 40.

Figure 11:
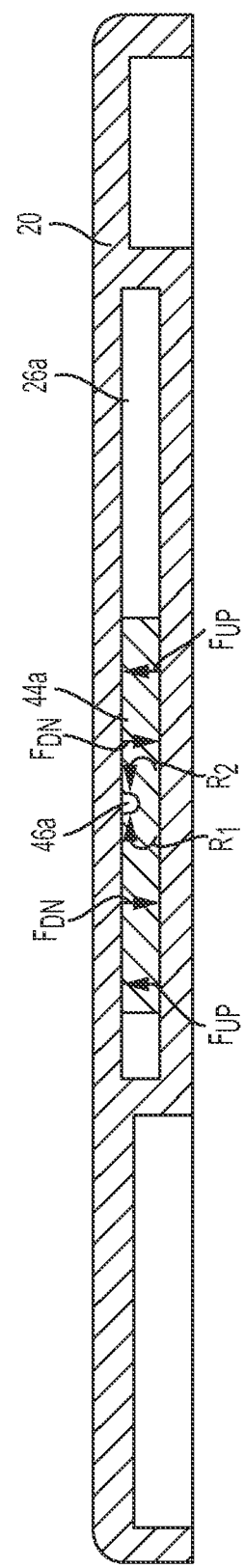
FIG. 11 is a cross-sectional view of the surgical instrument positioning device of FIG. 1 taken along the line C-C.

The forces $F_1$, $F_2$ applied by the tracks 54a, 54b can also cause the slider 40 to bend about the U-shaped slots 46a, 46b, as indicated by arrows $R_1$, $R_2$ in FIG. 10. As the slider 40 bends, pivots, or flexes about the U-shaped slots 46a, 46b, the upper surfaces of the mating features 44a, 44b can be pressed against the upper surfaces of the grooves 26a, 26b (as shown by arrows $F_{UP}$ in FIG. 11), while the lower surfaces of the slider 40 can be correspondingly pressed against the lower surfaces of the grooves 26a, 26b (as shown by arrows $F_{DN}$ in FIG. 11). This flexed configuration of the slider 40 can create interference between the slider and the base 20 that restricts translational (e.g., sliding) movement of the slider 40 within the grooves 26a, 26b. Thus, the locking mechanism 60 can be designed to constrain the surgical instrument 80 in all degrees of freedom with a single motion of the locking tab 62.

In some embodiments, a single locking tab 62 can be included to restrain a surgical tool 80 across all degrees of freedom. In other embodiments, however, the device 10 can include multiple locking tabs 62 configured to restrict movement of the surgical instrument 80 in only a selected number of degrees of freedom (e.g., a separate locking tab to prevent translational motion along a length L of the base 20, a width W of the base, etc.). In still other embodiments, the device 10 can include a locking tab 62 (or locking mechanism actuating member) for every degree of freedom, such that each degree of freedom can be individually restricted. Still further, a person skilled in the art will recognize other configurations that can also be used to achieve the locked and unlocked configurations provided for herein without departing from the spirit of the present disclosure.

One skilled in the art will appreciate that the various components of device 10 can have any size, shape, and configuration that is appropriate given the size of the device 10 and the performance requirements of the procedure. For example, the slider 40 can have a variety of shapes and configurations, such as rectangular, circular, pentagonal, etc. The pivot joint 50 can have a variety of shapes and configurations, for example a dome shape, a pyramid shape, etc. The locking tab 62 of the locking mechanism 60 can have a variety of shapes and configurations, for example a "U" shape, a "C" shape, a "V" shape, etc. Further, the ball 70 can have a variety of shapes and configurations, for example a spherical shape, a dodecahedron shape, an icosahedron shape, etc. The particular shapes of the above noted components can, in some embodiments, be designed with the shapes of corresponding mating components in mind to achieve desired functional requirements.

Additionally, in some embodiments, the various components can be rigid, thereby providing additional support to any surgical instrument 80 inserted within a patient. Alternatively, the components of the device 10 can be flexible, or have any degree of rigidity required for a particular procedure. The components of the device 10 can be made from any suitable material, including, but not limited to, a metal (e.g. stainless steel, titanium, etc.), a rigid polymer, or a flexible polymer.

In an exemplary embodiment of a surgical procedure utilizing the device 10, a surgeon or other user can adhere, or otherwise position, the base 20 against tissue, e.g. a patient's skin. Note that the base 20 can be attached to, or positioned against, tissue using any of a variety of techniques including friction, adhesives, straps, suction, magnetism, etc. In one exemplary embodiment, the device 10 is positioned above the patient's abdomen. The surgeon can insert a surgical instrument 80 into the through-hole 72 of the ball 70, as shown in FIG. 1. In other embodiments, the instrument 80 can be preinstalled within the through-hole 72 at any point before positioning the base 20 against a patient. In some embodiments, the surgeon can adjust the angle of approach of the distal end of the instrument 80 and puncture the epidermis of the patient to insert the instrument 80 into the abdominal cavity. The surgeon can adjust the tool to achieve a desired orientation and position by moving the instrument in the various (e.g., six) degrees of freedom afforded by the device 10. Upon positioning the instrument 80 in a desired orientation, the surgeon can lock the device 10 such that the tool is fixed with regard to all degrees of freedom relative to the base 20. Locking the device 10 in this manner can allow the surgeon, or other user, to continue the procedure with both hands free as the device maintains the position of the instrument 80 unattended.

While the devices described herein can be particularly useful in minimally invasive procedures employing percutaneously inserted surgical instruments, the disclosed devices and methods can also be utilized in other forms of minimally invasive, open, and/or robot-assisted procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A surgical instrument positioning device, comprising:
   a base configured to be placed against tissue such that the base does not move relative thereto;
   a shuttle coupled to the base, the shuttle being configured to slide relative to the base along a first longitudinal axis that extends along a length of the base and a second longitudinal axis that extends along a width of the base, wherein the shuttle comprises a slider that is configured to slide within the base along the first longitudinal axis, a pivot joint configured to slide within the slider along the second longitudinal axis, and a lumen configured to receive an elongate shaft of a surgical instrument, and wherein an orientation of the lumen relative to the base can be polyaxially adjusted; and
   a locking mechanism that, upon actuation, prevents both sliding movement of the shuttle relative to the base and polyaxial adjustment of the orientation of the lumen relative to the base.

2. The device of claim 1, wherein the base includes an adhesive disposed on a surface thereof that is configured to be placed against tissue.

3. The device of claim 1, wherein the length and width of the base are greater than a thickness thereof.

4. The device of claim 1, wherein the locking mechanism is further configured to prevent translational or rotational movement of a surgical instrument received by the lumen relative to the lumen upon actuation.

5. The device of claim 1, wherein the locking mechanism is a single cam lock.

6. The device of claim 1, wherein the locking mechanism is configured to be actuated by a single motion to lock a surgical instrument received by the lumen across six degrees of freedom.

7. A surgical instrument positioning device, comprising:
   a base configured to be placed against tissue such that the base does not move relative thereto;
   a socket coupled to the base and longitudinally slidable in at least two directions relative to the base;
   a ball seated within the socket and including a lumen formed therein that is configured to receive an elongate shaft of a surgical instrument;
   a single locking mechanism that, upon actuation, prevents both movement of the ball within the socket and longitudinal sliding of the socket relative to the base; and
   a slider disposed within an opening of the base and longitudinally slideable within the opening relative to the base, wherein the socket is coupled to and longitudinally slidable within the slider, and wherein the single locking mechanism, upon actuation, further prevents longitudinal sliding of the slider relative to the base.

8. The device of claim 7, wherein the base includes an adhesive disposed on a surface thereof that is configured to be placed against tissue.

9. The device of claim 7, wherein a length and width of the base are greater than a thickness thereof.

10. The device of claim 9, wherein the socket is longitudinally slidable in a direction parallel to the length of the base and a direction parallel to the width of the base.

11. The device of claim 7, wherein the single locking mechanism is further configured to prevent translational or rotational movement of a surgical instrument received by the ball relative to the ball upon actuation.

12. The device of claim 7, wherein the single locking mechanism is a cam lock.

13. The device of claim 7, wherein the single locking mechanism is configured to be actuated by a single motion to lock a surgical instrument received by the ball across six degrees of freedom.

14. A surgical instrument positioning device, comprising:
   a base configured to be placed against tissue such that the base does not move relative thereto;
   a socket slidably disposed within a track within the base and longitudinally slidable in at least two directions relative to the base;
   a ball seated within the socket and including a lumen formed therein that is configured to receive an elongate shaft of a surgical instrument;
   a locking mechanism that, upon actuation, prevents both movement of the ball within the socket and longitudinal sliding of the socket relative to the base; and
   a slider coupled to the base and configured to longitudinally slide relative to the base, wherein the locking mechanism, upon actuation, deforms the slider to create an interference fit between the base and the slider to thereby prevent longitudinal sliding of the slider relative to the base.

15. The device of claim 14, wherein the base includes an adhesive disposed on a surface thereof that is configured to be placed against tissue.

16. The device of claim 14, wherein a length and width of the base are greater than a thickness thereof.

17. The device of claim 16, wherein the socket is longitudinally slidable in a direction parallel to the length of the base and a direction parallel to the width of the base.

18. The device of claim 14, wherein the locking mechanism is further configured to prevent translational or rotational movement of a surgical instrument received by the ball relative to the ball upon actuation.

19. The device of claim 14, wherein the locking mechanism is a single cam lock.

20. The device of claim 14, wherein the locking mechanism is configured to be actuated by a single motion to lock a surgical instrument received by the ball across six degrees of freedom.

* * * * *